United States Patent [19]

Kawata et al.

[11] Patent Number: 4,578,391
[45] Date of Patent: Mar. 25, 1986

[54] OILY COMPOSITIONS OF ANTITUMOR DRUGS

[75] Inventors: Hiroitsu Kawata, Saitama; Tadayoshi Ohmura, Niiza; Shunji Hasumi, Saitama; Yutaka Konno, Saitama; Masayoshi Aruga, Saitama; Seiki Tashiro, Kumamoto; Toshimitsu Konno, Kumamoto; Ken Iwai, Kumamoto, all of Japan

[73] Assignee: Yamanouchi Pharmaceutical Co., Ltd., Tokyo, Japan

[21] Appl. No.: 457,636

[22] Filed: Jan. 13, 1983

[30] Foreign Application Priority Data

Jan. 20, 1982 [JP] Japan .................................. 57-7997
Aug. 12, 1982 [JP] Japan ............................... 57-215049

[51] Int. Cl.⁴ .................... A61K 31/505; A61K 31/40
[52] U.S. Cl. ...................................... 514/256; 514/410
[58] Field of Search ...................... 424/274, 251, 180; 514/256, 410

[56] References Cited

U.S. PATENT DOCUMENTS

| | | | |
|---|---|---|---|
| 4,011,661 | 3/1977 | Sezaki et al. | 34/12 |
| 4,104,461 | 8/1978 | Fox et al. | 424/180 |
| 4,231,936 | 11/1980 | Nakano et al. | 548/422 |
| 4,261,989 | 4/1981 | Sasaki et al. | 424/244 |

Primary Examiner—Jerome D. Goldberg
Assistant Examiner—John W. Rollins
Attorney, Agent, or Firm—Burgess, Ryan & Wayne

[57] ABSTRACT

An oily composition of an antitumor drug comprising at least one sparingly oil soluble or water-soluble antitumor drug, at least one fat or oil, and at least one solubilizing adjuvant in an oily vehicle selected from the group consisting of crown ether, lecithin, polyethylene glycol, propylene glycol, vitamin E, polyoxyethylene alkylether, and sucrose esters of fatty acids.

15 Claims, No Drawings

OILY COMPOSITIONS OF ANTITUMOR DRUGS

FIELD OF THE INVENTION

This invention relates to a composition composed of an antitumor drug dissolved or emulsified in fats and oils and the object of this invention is to provide an oily composition of an antitumor drug capable of effectively treating various tumors.

BACKGROUND OF THE INVENTION

Hitherto, many preparations have been developed and marketed as antitumor drugs. However, with the exception of a few products, they are limited for oral administration and for intravenous adminstration. Also, a considerable number of these antitumor drugs may have an excellent antitumor activity but they cause harmful side effects.

Now, if an antitumor drug is orally or intravenously administered chemotherapy for, for example, the special neoplastic tissues, not only the therapeutic effect is low but also there is a possibility of causing a side effect to a living body since the antitumor drug diffuses into the whole body. For solving these problems, a preparation which is prepared by carrying an antitumor drug on a carrier of low toxicity having an affinity for tissues and retentivity and can be directly administered into organ-distributing blood vessels and/or lymphatics has been proposed. However, as suitable carriers, there are known liposome, erythrocyte, DNA, fibrinogen, albumin, albumin microspheres, synthetic polymers, and fats and oils but such preparations which are practically used are only the preparations on antitumor drugs showing oil-solubility by themselves, such as a sesame oil solution of epitiostanol, etc. Other many important antitumor drugs which are insoluble in oil have not yet been practically used at present since an effective solubilizing means in an oily vehicle for fats and oils has not been found.

SUMMARY OF THE INVENTION

The inventors have investigated to dissolve water-soluble or sparingly oil-soluble antitumor drugs in fats and oils at a necessary concentration in various ways. As the results of the investigation, the inventors have succeeded in attaining the invention based on the discovery that it is possible to dissolve the foregoing antitumor drug into fats and oils by incorporating a specific solubilizing adjuvant in an oily vehicle (hereunder this is mentioned as "solubilizer").

That is, the invention is an oily composition of an antitumor drug comprising at least one sparingly oil-soluble or water-soluble antitimor drug, at least one fat or oil and at least one solubilizer selected from crown ether, lecithin, polyethylene glycol, propylene glycol, vitamin E, polyoxyethylene alkyl ether, and sucrose esters of fatty acids.

DESCRIPTION OF THE PREFERRED EMBODIMENT

As the sparingly oil-soluble or the water-soluble antitumor drugs used in this invention, there are Carmofur (HCFU), Fluorouracil (5-FU), Mitomycin C, aclarubicin hydrochloride (Acracinomycin A), ancitabine (cyclocytidine), etc. These antitumor drugs are used alone or as a mixture.

As fats and oils used in this invention, there are a strong iodized oil (the 9th Japanese Pharmacopoeia); an iodized oil (the 9th Japanese Pharmacopoeia); an iodized poppy seed oil fatty acid ethylester (Lipiodol Ultra-Fluide, trade name, made by Andre Guerbet); unsaturated higher fatty acids such as linoleic acid, linolenic acid, oleic acid, etc., and the esters thereof; the iodides of the foregoing unsaturated higher fatty acids; vegetable oils such as sesame oil, etc.; ODO (trade name of medium chain fatty acid glyceride, made by Nisshin Seiyu K. K.), etc.

Also, practical examples of the aforesaid solubilizer used in this invention are as follows. That is, as the crown ether, it is preferred to use 18-crown-6, dibenzo-18-crown-6, dicyclohexyl-18-crown-6, dibenzo-24-crown-8, dicyclohexyl-24-crown-8, or 15-crown-5; as the lecithin, it is preferred to use soybean lecithin, egg yolk lecithin, etc.; and as the polyethylene glycol (PEG), it is preferred to use a liquid type of polyethylene glycol, in particular PEG 400. As the polyoxyethylene alkylether, it is suitable to use Renex (trade name, made by Atlas Powder Co.). Also, as Renex, "Renex 35" which is a complex of polyoxyethylene alkylether and urea can be preferably used. Also, as sucrose esters of fatty acids, the esters having an HLB of lower than 10 are used. Examples of the esters are Ryoto Sugar Esters S-370, S-570, S-770, S-970, etc., (trade names) (In these marks, S stands for stearic acid, the number of the 3rd figure, e.g., 3, 5, etc., shows the HLB value, and the number of the 1st and the 2nd figure e.g. 70 etc. shows the content (%)of stearic acid.).

The composition of this invention is prepared as follows. That is, when an antitumor drug can be dissolved in a solubilizer at room temperature or by heating, the antitumor drug is first dissolved in a solubilizing adjuvant and the solution is dissolved in a fat or oil, or these three components are simultaneously mixed with each other and the mixture is stirred to dissolve the antitumor drug. Also, when an antitumor drug is sparingly soluble in a solubilizer or loses its stability by heating, (a) the antitumor drug and a solubilizer are first dissolved in a suitable solvent and after distilling off the solvent, the solid dispersion thus formed is dissolved in a fat or oil under stirring (solvent method), (b) the antitumor drug, a solubilizer and a fat or oil are dissolved in a proper organic solvent and then the solvent is distilled off, or (c) the foregoing three components are simultaneously mixed with each other and stirred to dissolve the antitumor drug. In this case, any organic solvents which can dissolve the foregoing conponents can be used. Also when a solubilizer has a surface activity as, for example, lecithin, water is added to the antitumor drug and lecithin, the mixture is emulsified by stirring, and after removing water from the emulsion, the residue may be dispersed (emulisfied) in a fat or oil. In this case, it sometimes happens that the composition (emulsion) obtained is separated into two layers but this is not based on recrystalization of the antitumor drug but is based on lecithin and the uniform emulsion can be easily obtained by shaking, if necessary, under heating. Thus, the compositions of this invention include not only solutions or an antitumor drug in fats and oils but also the emulsion of an antitumor drug in fats and oils. In addition, in the foregoing solvent method, the solid dispersion of the antitumor drug in the solubilizer can be used as a dissolution type preparation which is dissolved in a fat or oil with stirring in practical use. At dissolving the preparation with stirring, it is preferred to use a stirring mixer, anultra sonicator bath, etc.

The ratio of the antitumor drug to the solubilizer in the composition of this invention depends upon the kind of the solubilizer but the proportion of the solubilizer is generally 0.05 to 1000 parts by weight, preferably 1 to 100 parts by weight per 1 part by weight of the antitumor drug.

The composition of this invention may be administered as it is or may be administered after adding thereto proper compounding components for preparation or other medicaments.

Also, if necessary, the composition of this invention may be used after being sterilized in an ordinary manner.

Then, for providing the usefulness of the composition of this invention, the antitumor effect of the composition for rabbits is explained together with the experimental procedure.

Experimental procedure

Using 22 New Zealand White rabbits, 0.2 ml each of a suspension containing 1000,000 to 1500,000 $VX_2$ cancerous cells in 1 ml was injected in the subserosal tissue of the left lateral lobe of the liver of each rabbit and when the diameter of the tumor became about 2 cm after two weeks since the injection of the suspension the rabbits were subjected to the following experiment.

Groups 1: Mitomycin C (MMC) oil solution-administered group (12 rabbits). The Mitomycin C (MMC) oil solution obtained in Example 16 was diluted twice with Lipiodol Ultra-Fluide and 0.2 ml of the diluted solution was administered into the common hepatic artery of each rabbit under the laparotomy.

Group 2: Lipiodol -adminstered group (6 rabbits) (control).

Lipiodol (0.2 ml) was administered into the common hepatic artery of each rabbit under the laparotomy.

Group 3: Aqueous Mitomycin C solution-administered group (4 rabbits) (control).

A solution (1 ml) containing 2 mg/ml of Mitomycin C was administered into the common hepatic artery of each rabbit under laparotomy.

In regard to Group 1 and Group 2, after one week since the administration, the rabbit was sacrificed. And the dissected liver was cut into 0.5 cm thick slices. Then Softex radiographs and microscopic specimens of the (those) slices were obtained.

In the conditions for the Softex radiograph, a Softex apparatus MR was used, the distance was 34 cm, the tube potential was 25-30 KVP, and the exposure time was 1-1.5 minutes.

In regard to Group 3, liver sections dissected 1 week post operation as in Group 1 and Group 2 were stained with Hematoxylin and Eosin, and examined. In addition, besides Group 2 and Group 3 as a control experiment, a dosage form obtained by adding a Mitomycin C powder for aqueous injection to Lipiodol was investigated. But Mitomycin C was not dissolved in Lipiodol. When the preparation is intraarterially injected, the particles of Mitomycin C will cause an embolism of peripheral blood vessels, which shows that the preparation is not suitable for practical use.

Experimental result

Group 1: The neoplastic tissue was softened at the sacrifice, and the size of them were same as that seen at the time of intraarterial injection of the oil solution.

Lipiodol on the Softex radiograph was observed limited to the neoplastic tissue.

On the cut surface, the neoplastic tissues changed grayish white and soft. Histologically, the most parts of the neoplastic tissue were degenerative and necrotic and at the periphery of tumor, a marked inflammatory cell infiltration, particularly lymphocytic infiltration was observed.

Group 2: Neoplastic tissues were white, elastic hard and have definitely grown compared to that examined previously when we administered Lipiodol.

On the Softex photograph, Lipiodol was observed in tumor to an extent of Group 1. There was a portion showing histologically very slight degenerative changes but in the greater portion viable $VX_2$ cancerous cells were observed and an inflammatory cell infiltration was not observed.

Group 3: In spite of that the dose of Mitomycin C in the group was 10 times larger than that in Group 1, the antitumor effect to $VX_2$ cancer was scarcely observed on three rabbits. And in one rabbit, diffuse degenerative change was observed in the neoplastic tissues, but viable cancerous cells were also observed.

From the above experimental results, it is clear that the compositions of this invention have remarkable antitumor effect.

Then, the invention will be more practically explained by the following examples.

EXAMPLE 1

To 100 mg of ancitabine was added 100 mg of Renex 35 and then the mixture was heated on a steam bath to provide a homogeneous transparent liquid. Then, by adding 3 ml of linoleic acid to the liquid followed by shaking and allowing to stand the mixture at room temperature, a transparent liquid was obtained.

EXAMPLE 2

By shaking a mixture of 20 mg of Fluorouracil, 2,000 mg of PEG 400, and 3 ml of linoleic acid, a transparent liquid was obtained.

EXAMPLE 3

By shaking a mixture of 2 mg (potency) of Mitomycin C, 1 ml of PEG 400, and 1.5 ml of linoleic acid, a transparent liquid was obtained.

EXAMPLE 4

To 2 mg (potency) of Mitomycin C were added 100 mg of α-tocopherol and 4 ml of methanol. After dissolving by shaking the mixture, methanol was distilled off under reduced pressure by means of a rotary evaporator. Futhermore, after drying in vacuo the residue overnight at room temperature, 2 ml of linoleic acid was added to the residue and then the mixture was immersed in an ultra sonicator bath for 5 minutes to provide a clear and transparent liquid.

EXAMPLE 5

To 2 mg (potency) of Mitomycin C were added 1.5 ml of propylene glycol and 1.5 ml of linoleic acid, and then the mixture was shaken well to provide a transparent liquid.

EXAMPLE 6

In 20 ml of water was dissolved 50 mg of Fluorouracil and then 1,000 mg of soybean lecithin was dispersed in the aqueous solution of Fluorouracil thus obtained. The dispersion was heated to 50° C. and then water was distilled off under reduced pressure by means of a rotary evaporator. Futhermore, the residue was dried in vacuo overnight at room temperature on phosphorus pentaoxide. To the residue was added 2.5 ml of linoleic acid and the mixture was immersed in an ultra sonicator bath for 5 minutes to provide a homogeneous emulsion.

EXAMPLE 7

In 1.5 ml of linoleic acid was dissolved 25 mg of soybean lecithin in an ultra sonicator bath and the solution thus obtained was added to 2 mg (potency) of Mitomycin C. By immersing the mixture in an ultra sonicator bath for 5 minutes, a clear and transparent solution was obtained.

EXAMPLE 8

To 50 mg of ancitabine (base) were added 250 mg of soybean lecithin and then 20 ml of water and after immersing the mixture in an ultra sonicator bath for 5 minutes, water was distilled off under reduced pressure at 50° C. Thereafter, the residue was further dried in vacuo overnight at room temperature on phosphorus pentaoxide and 1.5 ml of linoleic acid was added to the residue to provide a homogeneous emulsion.

EXAMPLE 9

In 10 ml of chloroform were dissolved 2 mg (potency) of Mitomycin C and 100 mg of egg yolk lecithin and after adding 3 ml of sesame oil to the solution, the mixture was stirred. When chloroform was completely distilled off under reduced pressure at 30° C. using a rotary evaporator, a clear and transparent liquid was obtained.

EXAMPLE 10

In 4 ml of acetone were dissolved 2 mg (potency) of Mitomycin C and 20 mg of 18-crown-6 and then acetone was evaporated off to dryness. The residue thus obtained was further dried in vacuo overnight at room temperature and after adding thereto 2.0 ml of linoleic acid, the mixture was shaken well to provide a clear and transparent solution.

EXAMPLE 11

In 20 ml of methanol were dissolved 50 mg of ancitabine (base) and 150 mg of 18-crown-6. Methanol was evaporated to dryness and the residue was further dried in vacuo overnight at room temperature. Then, 1.5 ml of linoleic acid was added to the residue. The mixture was immersed in an ultra sonicator bath for 5 minutes to provide a clear and transparent solution.

EXAMPLE 12

In 20 ml of methanol were dissolved 50 mg of ancitabine hydrochloride and 150 mg of 18-crown-6. Methanol was evaporated to dryness and the residue was further dried in vacuo overnight at room temperature. Then, 1.5 ml of linoleic acid was added to the residue. The mixture was immersed in an ultra sonicator bath for 5 minutes to provide a clear and transparent solution.

EXAMPLE 13

In 2 ml of acetone were dissolved 10 mg of Fluorouracil and 50 mg of 18-crown-6 and acetone was evaporated to dryness. After further dried in vacuo the residue overnight at room temperature, 1.5 ml of linoleic acid was added to the residue.
The mixture was shaken to provide a clear and transparent solution.

EXAMPLE 14

To 90 mg of Carmofur were added 3 ml of Lipiodol Ultra-Fluide and 180 mg of 18-crown-6 and after heating the mixture to about 50° C. to dissolve, the solution was allowed to stand at room temperature to provide a clear and transparent solution.

EXAMPLE 15

In 5 ml of chloroform were dissolved 100 mg Carmofur and 300 mg of 18-crown-6 and after distilling off chloroform under reduced pressure at 30° C., the residue was dried in vacuo for 18 hours. To the residue was added 3 ml of Lipiodol Ultra-Fluide and the mixture was shaken to provide a clear and transparent solution.

EXAMPLE 16

In 110 ml of chloroform were dissolved 26 mg (potency) of Mitomycin C and 2.6 g of egg yolk lecithin and after distilling off chloroform under reduced pressure at 30° C., the residue was further dried in vacuo for 2 hours at 30° C. To the residue was added 13 ml of Lipiodol Ultra-Fluide and the mixture was shaken lightly to provide a clear and transparent liquid.

EXAMPLE 17

In 5 ml of chloroform were dissolved 100 mg of Carmofur, 250 mg of 18-crown-6, and 100 mg of soybean lecithin and after distilling off chloroform under reduced pressure at 30° C., the residue was further dried in vacuo for 18 hours at room temperature. To the residue was added 3 ml of Lipiodol Ultra-Fluide and the mixture was shaken to provide a clear and transparent solution.

EXAMPLE 18

In 5 ml of chloroform were dissolved 2 mg (potency) of Mitomycin C and 200 mg of egg yolk lecithin and after distilling off chloroform under reduced pressure at 30° C., the residue was further dried in vacuo for 2 hours at 30° C. To the residue was added 2 ml of strong iodized oil (the 9th Japanese Pharmacopoeia) and the mixture was shaken to provide a clear and transparent liquid.

EXAMPLE 19

In 10 ml of chloroform were dissolved 2 mg (potency) of Mitomycin C and 200 mg of egg yolk lecithin and after distilling off chloroform under reduced pressure at 30° C., the residue was further dried in vacuo overnight at room temperature. To the residue were added 20 mg of aclarubicin hydrochloride and then 2.5 ml of linoleic acid followed by stirring to provide a clear and transparent liquid.

What is claimed is:

1. An oily composition of an effective amount of an antitumor drug comprising a sparingly oil-soluble or water-soluble antitumor drug selected from the group consisting of carmofur, 5-fluorouracil, mitomycin C, aclarubicin hydrochloride, ancitabine, and ancitabine hydrochloride, an effective amount of a fat or oil, and an effective amount of a solubilizing adjuvant selected from the group consisting of crown ethers, lecithin, polyethylene glycol, propylene glycol, vitamin E, polyoxyethylene alkylether, and sucrose esters of fatty acids, the proportion of said solubilizing adjuvant being within the range of 0.05 to 1000 parts by weight per part by weight of said antitumor drug.

2. A composition as claimed in claim 1, wherein the fat or oil is selected from the group consisting of iodized poppy seed oil fatty acid ethylester, iodized oil, strong iodized oil, unsaturated higher fatty acids and esters and iodides thereof, vegetable oils, and a medium chain fatty acid glyceride.

3. A composition as claimed in claim 2, wherein said unsaturated higher fatty acids are selected from the group consisting of oleic acid, linoleic acid, and linolenic acid.

4. A composition as claimed in claim 1, wherein the fat or oil is selected from iodized poppy seed oil fatty acid ethylester, strong iodized oil or iodized oil.

5. A composition as claimed in claim 1, wherein the fat or oil is a combination of (a) a member selected from iodized poppy seed oil fatty acid ethylester, strong iodized oil or iodized oil, and (b) a member selected from linoleic acid, oleic acid, or linolenic acid.

6. A composition as claimed in claim 1, wherein the solubilizing adjuvant is lecithin, and the fat or oil is iodized poppy seed oil fatty acid ethylester.

7. A composition as claimed in claim 1, wherein the solubilizing adjuvant is lecithin, and the fat or oil is selected from iodized poppy seed oil fatty acid ethylester, strong iodized oil or iodized oil.

8. A composition as claimed in claim 1, wherein the solubilizing adjuvant is selected from lecithin, vitamin E or sucrose esters of fatty acids, and the fat or oil is selected from iodized poppy seed oil fatty acid ethylester, strong iodized oil or iodized oil.

9. A composition as claimed in claim 1, wherein the solubilizing adjuvant is a combination of (a) a member selected from lecithin, vitamin E or sucrose esters of fatty acids, and (b) a member selected from propylene glycol, polyethylene glycol, polyoxyethylene alkylether or crown ethers, and the fat or oil is selected from iodized poppy seed oil fatty acid ethylester, strong iodized oil or iodized oil.

10. The oily composition of claim 1 wherein said antitumor drug is carmofur.

11. The oily composition of claim 1 wherein said antitumor drug is 5-fluorouracil.

12. The oily composition of claim 1 wherein said antitumor drug is mitomycin C.

13. The oily composition of claim 1 wherein said antitumor drug is aclarubicin hydrochloride.

14. The oily composition of claim 1 wherein said antitumor drug is ancitabine.

15. The oily composition of claim 1 wherein said antitumor drug is ancitabine hydrochloride.

* * * * *